(12) United States Patent
Taylor (10) Patent No.: US 6,814,724 B2
(45) Date of Patent: Nov. 9, 2004

(54) WATER PURIFICATION PACK

(75) Inventor: Michael A. Taylor, Napa, CA (US)

(73) Assignee: PrisMedical Corporation, Napa, CA (US)

( * ) Notice: Subject to any disclaimer, the term of this patent is extended or adjusted under 35 U.S.C. 154(b) by 0 days.

(21) Appl. No.: 10/339,702

(22) Filed: Jan. 8, 2003

(65) Prior Publication Data

US 2003/0105435 A1 Jun. 5, 2003

Related U.S. Application Data

(60) Division of application No. 09/364,631, filed on Jul. 30, 1999, now Pat. No. 6,719,745, which is a continuation-in-part of application No. 09/277,448, filed on Mar. 26, 1999, now Pat. No. 6,274,103.

(51) Int. Cl.[7] ............................................. A61B 19/00
(52) U.S. Cl. .................................. 604/406; 210/323.1
(58) Field of Search ................................ 604/403, 406, 604/500, 507, 82, 905; 210/195.1

(56) References Cited

U.S. PATENT DOCUMENTS

| | | | |
|---|---|---|---|
| 3,730,349 A | 5/1973 | Herrmann | |
| 4,231,872 A | 11/1980 | Keil | |
| 4,280,912 A | 7/1981 | Berry, III et al. | |
| 4,495,067 A | 1/1985 | Klein et al. | |
| 4,756,838 A | 7/1988 | Veltman | |
| 4,871,463 A | 10/1989 | Taylor et al. | |
| 5,071,558 A | 12/1991 | Itob | |
| 5,084,558 A | 1/1992 | Rausch et al. | |
| 5,110,479 A | 5/1992 | Frommer et al. | |
| 5,259,954 A | 11/1993 | Taylor | |
| 5,264,555 A | 11/1993 | Shorr et al. | |
| 5,395,323 A | 3/1995 | Berglund | |
| 5,494,585 A | 2/1996 | Cox | |
| 5,685,980 A | 11/1997 | Patapoff et al. | |
| 5,725,777 A | 3/1998 | Taylor | |

OTHER PUBLICATIONS

PCT International Search Report, 2 pp. (Courtesy Copy).
PCT International Search Report, 3 pp. (Courtesy Copy).

Primary Examiner—Anhtuan T. Nguyen
(74) Attorney, Agent, or Firm—Knobbe, Martens, Olson & Bear LLP (57) ABSTRACT

An apparatus and methods are disclosed for purifying fluid, such as potable water, to quality levels suitable for medical application, particularly to applications involving injection of the fluid into a human body. The apparatus comprises a portable purification pack constructed for a single use. The pack houses depth filtration, activated carbon, mixed bed ion exchange resins and terminal filtration stages in series. The terminal filter comprises a fine (microfiltration or ultrafiltration), permeable membrane, treated with an endotoxin-binding chemistry. In contrast with semi-permeable osmotic membranes, the permeable membrane produces high flow rates at relatively low pressures, while still safely purifying fluid to injection quality.

20 Claims, 9 Drawing Sheets

WATER PURIFICATION PACK

CROSS-REFERENCE TO RELATED APPLICATION

This application is a divisional of U.S. application Ser. No. 09/364,631, filed Jul. 30, 1999, now U.S. Pat. No. 6,719,745 (the disclosure of which is incorporated herein by reference), which is a continuation-in-part of U.S. application Ser. No. 09/277,448 filed Mar. 26, 1999, now U.S. Pat. No. 6,274,103, issued Aug. 14, 2001.

FIELD OF THE INVENTION

The invention generally relates to water purification, and more particularly to devices and methods for purifying water to a quality suitable for medical applications.

BACKGROUND OF THE INVENTION

Various medical conditions require treatments that call for the injection of fluids into the human body. For example, severe trauma to the human body often involves significant loss of bodily fluids. Additionally, illnesses often cause diarrhea followed by dehydration and ion imbalance. In order to rehydrate the individual, injection of an intravenous saline or dextrose solution is required. Other medical applications (e.g., wound irrigation) require similar fluid purity levels.

An example of the need for injection of fluids into the body is in the area of dialysis. Treatments for patients having substantially impaired renal function, or kidney failure, are known as "dialysis." Either blood dialysis ("hemodialysis") or peritoneal dialysis methods may be employed. Both methods essentially involve the removal of toxins from body fluids by diffusion of the toxins from the body fluids into a toxin free dialysis solution. Peritoneal dialysis can be performed without complex equipment and in a patient's home. In the peritoneal dialysis process, the patient's peritoneal cavity is filled with a dialysate solution. Dialysates are formulated with a high concentration of the dextrose, as compared to body fluids, resulting in an osmotic gradient within the peritoneal cavity. The effect of this gradient is to cause body fluids, including impurities, to pass through the peritoneal membrane and mix with the dialysate. By flushing the dialysate from the cavity, the impurities can be removed.

Due to indirect contact with bodily fluids through bodily tissues, rather than direct contact with blood, the dextrose concentration needs to be considerably higher in peritoneal dialysis than in hemodialysis, and the treatment is generally more prolonged. Peritoneal dialysis may be performed intermittently or continuously. In an intermittent peritoneal dialysis (IPD) procedure, the patient commonly receives two liters of dialysate at a time. For example, in a continuous ambulatory peritoneal dialysis (CAPD) procedure, the peritoneal cavity is filled with two liters of dialysate and the patient is the free to move about while diffusion carries toxins into the peritoneal cavity. After about 4–6 hours, the peritoneum is drained of toxified dialysate over the course of an hour. This process is repeated two to three times per day each day of the week. Continuous Cycle Peritoneal Dialysis (CCPD) in contrast, involves continuously feeding and flushing dialysate solution through the peritoneal cavity, typically as the patient sleeps.

Because peritoneal dialysates are administered directly into the patient's body, it is important that the dialysis solution maintains the correct proportions and concentrations of reagents. Moreover, it is impractical to formulate and mix dialysis solutions on site at the typical location of administration, such as the patient's home. Accordingly, peritoneal dialysates are typically delivered to the site of administration in pre-mixed solutions.

Unfortunately, dialysis solutions are not stable in solutions over time. For example, dextrose has a tendency to caramelize in solution over time, particularly in the concentrations required in the peritoneal dialysis context. To prevent such caramelization, peritoneal dialysis solutions are typically acidified, such as with hydrochloric acid, lactate or acetate, to a pH between 4.0 and 6.5. The ideal pH level for a peritoneal dialysate, however, is between 7.2 and 7.4. While achieving the desired goal of stabilizing dextrose in solution, the pH of acidified peritoneal dialysis solutions tends to damage the body's natural membranes after extended periods of dialysis. Additionally, the use of acidified peritoneal dialysates tends to induce acidosis in the patient.

Bicarbonates introduce further instability to dialysis solutions. The most physiologically compatible buffer for a peritoneal dialysate is bicarbonate. Bicarbonate ions react undesirably with other reagents commonly included in dialysate solutions, such as calcium or magnesium in solution, precipitating out of solution as insoluble calcium carbonate or magnesium carbonate. These insolubles can form even when the reactants are in dry form. When occurring in solution, the reactions also alter the pH balance of the solution through the liberation of carbon dioxide ($CO_2$). Even in the absence of calcium or magnesium salts, dissolved sodium bicarbonate can spontaneously decompose into sodium carbonate and $CO_2$, undesirably lowering the solution's pH level.

Accordingly, a need exists for improved methods and devices for formulating solutions for peritoneal dialysis. Desirably, such methods and devices should avoid the problems of non-physiologic solutions and incompatibility of dialysate reagents, and also simplify transportation, storage and mixing of such dialysates. One aspect of this problem is the need for mechanisms for safely and completely mixing constituents of dialysates in diluent at the point of administration. Another aspect of this problem is the need for producing injectable quality water or other diluent at the point of administration.

It is often advantageous to provide purified fluid independently of other constituents in the injected fluid. In many situations, independent provision of purified water simplifies transport and storage of solution constituents. In the case of peritoneal dialysis, preparing dialysate solution from dry reagents and independently provided pure water also minimizes the time for which unstable solutions must be stored prior to administration. Similarly, many other unstable solutions should be prepared soon before administration, preferably at the site of administration.

On site purification of fluids is also advantageous in a number of other medical applications, including intravenous injection, intramuscular injection, orally administered fluids, wound irrigation, use in instrument cleaning solutions, and general employment by immuno-compromised individuals (e.g., AIDS patients, geriatrics, etc.).

While separating provision of injectable quality fluid from other constituents can simplify transportation and delay production of unstable solutions, transporting purified water to the site of administration, even if produced and shipped separately from dry reagents, can represent considerable costs, as well as introducing opportunities for contamination. Transportation costs and contamination are particularly problematic when fluids are to be administered outside of a controlled hospital or clinic environment. Problems are even further exacerbated in lesser-developed countries, such as in the Indian subcontinent and Africa. Even in a hospital setting, the ability to convert available water into injectable quality water on site can reduce transportation and storage costs as well as avoiding the risk of contamination during transportation and storage.

Therefore, a need exists for a method and apparatus that allow preparation of injectable quality fluid from available fluid. Desirably, the apparatus should be transportable and convenient for on-site use in remote locations.

SUMMARY OF THE INVENTION

In satisfying the aforementioned needs, the embodiments described herein provide a portable apparatus and method for purifying fluid to levels suitable for medical applications, including injection into the human body.

In accordance with one aspect of the present invention, a portable apparatus is provided for producing injectable quality fluid. The apparatus includes a housing that defines a fluid flow path from an inlet port to an outlet port. A depth filtration stage, an organic filtration component, a deionization resin bed and a permeable membrane are held within the housing along the fluid flow path. The permeable membrane has a porosity of less than about 0.5 $\mu$m and is configured to retain endotoxins.

In accordance with another aspect of the present invention, a water purification pack for producing injectable quality water includes a container. The container defines a flow-through path from an inlet to an outlet with an average cross-sectional area of less than about 20 square inches. The container houses purification elements within the path, including a permeable membrane having a porosity of no more than about 0.5 $\mu$m. The purification elements provides a back-pressure low enough to allow fluid flow greater than about 30 mL/min under a feed pressure of between about 5 psi and 10 psi.

In accordance with another aspect of the invention, a method is provided for producing injectable quality of water. The method includes providing a portable purification pack with a housing surrounding purification elements in series. Non-sterile water is provided to an inlet of the housing under a feed pressure of less than about 20 psi. The water passes through the purification elements. Purified water exits from an outlet of the housing. The purified water has an organic content, conductivity, pH level and particulate contamination level suitable for injection into the human body.

In accordance with another aspect of the invention, a method is provided for producing fluid for medical applications. The method includes providing a portable housing. Non-sterile fluid passes through the housing. Particulate contamination, organic matter, dissociated ions, microbes and endotoxins from the feed fluid are retained within purification elements in the housing. Fluid suitable for medical applications is then output from the housing.

BRIEF DESCRIPTION OF THE DRAWINGS

These and other aspects of the invention will be apparent to the skilled artisan in view of the Detailed Description and claims set forth below, and in view of the appended drawings, which are meant to illustrate and not to limit the invention, and wherein:

DETAILED DESCRIPTION OF THE PREFERRED EMBODIMENT

While the illustrated embodiments are described in the context of a particular application, i.e., peritoneal dialysis, the skilled artisan will find application for the apparatus and methods for producing injectable quality fluid in a variety of medical applications. Moreover, the apparatus and methods for producing "injectable quality" fluids will have applications beyond the medical field, wherever similarly pure water is desirable. The fluid purification unit described herein has particular utility when connected in series upstream of fluid collection/delivery devices, such as the illustrated mechanism for mixing dry reagent as purified diluent flows through.

System for Preparing Peritoneal Dialysis Solution

Figure 1:
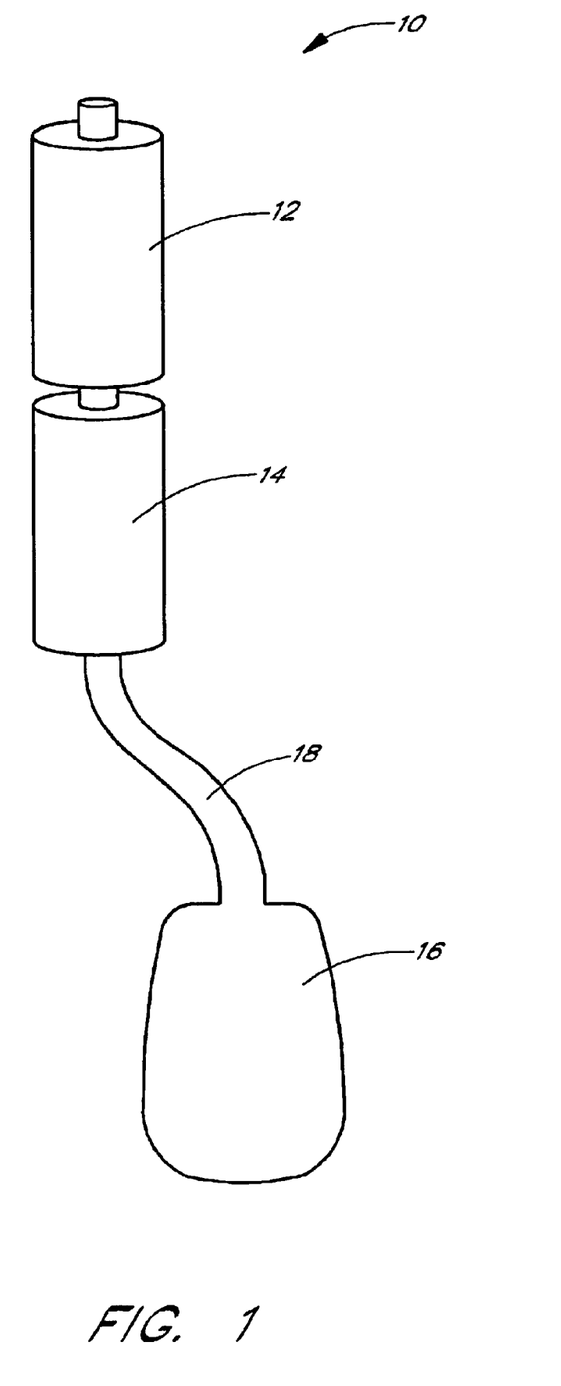
FIG. 1 is a schematic side perspective view of a system for producing peritoneal dialysate or other medical solutions.

FIG. 1 illustrates a system 10 for producing solutions suitable for injection into the human body. A diluent or fluid purification pack 12, as described in more detail below, is connected upstream of a reagent cartridge 14. The cartridge 14, in turn, is in fluid communication with a solution reservoir 16 via a tube 18. As also set forth in more detail below, purified diluent is provided from the pack 12 to the reagent cartridge 14, wherein the dry reagents are dissolved and solution is delivered to the reservoir 16. Alternatively, the solution can be delivered directly to the patient's body.

In the illustrated embodiment, the solution comprises peritoneal dialysis solution. The cartridge 14 advantageously houses dry or lyophilized formulations of reagents suitable for peritoneal dialysis. Desirably, the solution is formed immediately prior to delivery to the patient's peritoneal cavity, such that the dialysate need not be stored in solution form for extended periods, and little opportunity exists undesirable reactions within the solution prior to delivery.

The cartridge 14 defines fluid flow paths through the dry reagents, by way of porous elements therebetween, enabling dry storage in confined reagent beds while also enabling dissolution simply by passing diluent through the housing. Two preferred versions of the cartridge 14 are described in more detail with respect to FIGS. 3–7, below.

The diluent purification pack 12 of the illustrated embodiment is capable of on-site purification of locally available fluid, such as tap water from a municipal water source. The preferred water purification pack is described in more detail with respect to FIG. 2 below.

Water Purification Pack

Figure 2:
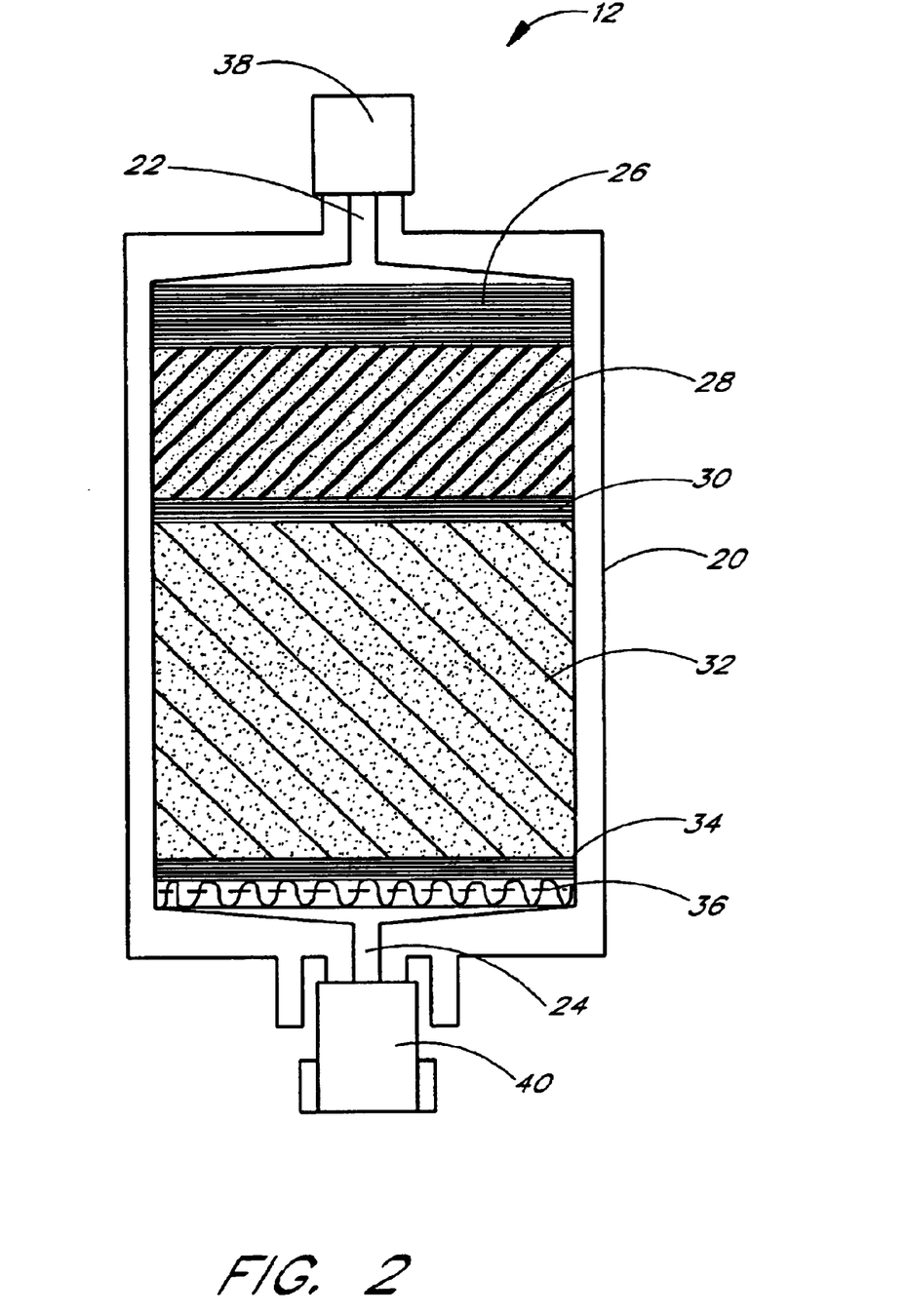
FIG. 2 is a schematic side sectional view of a fluid purification pack, constructed in accordance with one aspect of the present invention.

Referring to FIG. 2, the preferred fluid purification pack 12 is capable of purifying water or other liquid diluent to the standards required for injection into a patient, e.g., for peritoneal dialysis applications. Advantageously, available water, preferably potable water, can be introduced to the system, and is purified as it flows through the pack. The purified water can be delivered, for example, directly to the reagent cartridge 14 (FIG. 1), to a storage or collection container for short-term storage or transportation or direct connection to line another delivery device, such as a wound irrigation pump. Accordingly, bulky purified water need not be stored long in advance of its need or transported great distances to the point of administration. Complex machinery for purifying water is also obviated.

In order to serve as a diluent for injection into the human body, or for similar applications, the independently provided water must be highly purified. The U.S. Pharmacopoeia provides processes for producing sterile water for injection. The preferred water pack 12 also produces water of a quality suitable for injection, preferably equivalent to or surpassing the quality produced by the U.S. Pharmacopoeia processes. Water purified through the pack thus preferably meets or exceeds the U.S. Pharmacopoeia's standards for Sterile Water for Injection, including sterility, pH, ammonia, calcium, carbon dioxide, chloride, sulfate and oxidizable substances tests. In particular, injectable quality water or other fluid produced by the illustrated water purification pack 12 exhibits the following characteristics: a very low level of total organic carbon, preferably less than about 1 ppm and more preferably less than about 500 ppb; low conductivity, preferably less than about 5.0 $\mu$Siemens (2.5 ppm) and more preferably less than about 2.0 $\mu$Siemens (1 ppm); near neutral pH, preferably between about 4.5 and 7.5, and more preferably between about 5.0 and 7.0; very low particulate concentration, preferably fewer than less than about 12 particles/mL of particles $\geq 10$ $\mu$m, more preferably less than about 6 particles/mL of such particles, and preferably less than about 2 particles/mL of particles $\geq 25$ $\mu$m, more preferably less than about 1 particle/mL of such particles; and low endotoxin levels, preferably less than about 0.25 endotoxin units (EU) per mL (0.025 ng/mL), more preferably less than about 0.125 EU/mL (0.0125 ng/mL) with a 10:1 EU/ng ratio.

Conventionally, purifying non-sterile fluid to such stringent quality standards, particularly for introduction into the human body, has called for extensive mechanical filtration and/or distillation, pumping, distribution and monitoring systems. These complex mechanisms can safely and economically produce large volumes of sterile water to injectable quality. Such mechanisms, however, occupy considerable space at a central location and necessitate even more space for storing purified water closer to the site of administration. Moreover, conventional water purification mechanisms are not conducive to employment in a portable apparatus for use in the field.

U.S. Pat. No. 5,725,777 to Taylor discloses a portable apparatus for purifying water to injectable quality. The apparatus includes several stages for purification, including multistage depth prefiltering, ultrafiltration fibers, reverse osmosis fibers, ion exchange resin and activated carbon in that order.

The reverse osmosis stage of Taylor '777 effectively purifies water to a high degree. Unfortunately, because reverse osmosis involves diffusing input water across a semi-permeable membrane, the rate of water production is very slow relative to the cross-section of the membrane. Even with the use of multiple reverse osmosis fibers with a high overall membrane surface area, diffusion is slow. In order to fully realize the advantages of portability, purified diluent should be rapidly produced at the time of administration. For acceptable rates using the apparatus of Taylor '777, however, high pressures (e.g., 40 to 75 psi) are applied across the semi-permeable membrane. Pumps and restrictor means for realizing these pressures reduce the versatility and portability of the overall system.

In the illustrated embodiment, the water or fluid purification pack 12 comprises a housing 20 with an axial inlet 22 and outlet 24. The housing 20 defines a flow path between the inlet 22 and outlet 24, with multiple purification stages along the flow path. The pack 12 is thus designed to purify fluid in the course of traveling, preferably in a linear path, through the housing 20.

The housing 20 is preferably formed of a suitable polymer, particularly polycarbonate, which aids in purifying water by binding endotoxins through charge interactions. Endotoxins are the organic by product of dead microorganisms, particularly the outer cell wall of bacteria. Although the term endotoxin is occasionally used to refer to any "cell-associated" bacterial toxin, it primarily refers to the lipopolysaccharide complex associated with the outer envelope of Gram-negative bacteria such as *E. coli, Salmonella, Shigella, Pseudomonas, Neisseria, Haemophilus*, and other leading pathogens. In high enough concentrations, particularly in critical applications such as intravenous injection, this organic matter can be toxic.

The pack 12 is configured for convenient portability. The skilled artisan will appreciate the fact that different sizes will safely produce different amounts of purified water. Thus, for an embodiment optimized for safely purifying 10 L of water, the outside dimensions of the housing 20 preferably include a length of less than or equal to about 6 inches from inlet 22 to outlet 24, and a width (diameter in the illustrated embodiment) of less than or equal to about 5 inches. The illustrated housing 20, designed for safely purifying 2 L of water, has a length of about 3 inches and a diameter of about 2.25 inches. Preferably, therefore, the fluid purification pack 12 has a cross-sectional area of less than about 20 sq. inches, more preferably less than about 4 sq. inches. Despite this small cross-section, the illustrated pack 12 can achieve high flux rates under pressures as low as about 5–10 psi.

The fluid purification pack 12 is also preferably configured to deliver a unit dose of purified fluid. The pack 12 thus is preferably designed for one-time use and to be discarded thereafter. As such, the sterility of the pack 12 can be assured, since the pack 12 will not be reused after seals at the inlet 22 and outlet 24 are broken. Several of the features described hereinbelow discourage or prevent recharging the water pack 12 for repeated use, as will be understood by the skilled artisan.

Downstream of the inlet 22 is a depth filter 26. The porosity limit of the illustrated depth filter 26 preferably ranges from about 1 micron ($\mu$m) to 10 $\mu$m, most preferably about 1 $\mu$m. The depth filter 26 is preferably formed of a porous polypropylene mesh in multiple layers, particularly two to four layers. Alternatively, the commercially available cellulose-based depth filters can be employed, as will be understood by one of ordinary skill in the art. In still other arrangements, ceramic or other known particle filtration material can be employed. Most preferably, the depth filter 26 comprises a series of depth filters (not shown) that successively filter out smaller and smaller particles. In the illustrated embodiment, four successive depth filters are included within the depth filtration stage 26, having porosities of about 100 μm, 40 μm, 10 μm and 1 μm in sequence from upstream end to downstream end.

Downstream of the depth filter 26 is an organic filtration stage 28, which can comprise a bed of granular carbon. In the illustrated embodiment, the organic filtration stage comprises a resin bed treated for retention of organic contaminants. The illustrated embodiment incorporates a form of styrene divinylbenzene commercially available from Rohm & Haas of Philadelphia, Pa. under the trade names Ambersorb 563. This component removes certain residual organic contaminants, such as endotoxins, as well as commonly used additives placed in municipally treated waters (e.g., chlorine, trihalomethanes and chloramine).

Adjacent to the downstream end of the organic filtration stage 28 is a restraint 30. The restraint 30 is a filter of controlled porosity, preferably also comprising a polypropylene mesh with a porosity of about 1–10 microns, more preferably about 1 micron. This component prevents passage of particulates shed by the organic filtration component 28, as well as providing a secondary assurance that insoluble particulates do not pass further through the water purification pack.

Adjacent to the downstream side of the restraint 30 is a deionization stage, preferably comprising a bed 32 of deionization resin beads. The resin bed 32 more preferably comprises a mixture of pharmaceutical grade resins with strong anion exchanger (cation-impregnated) and strong cation exchanger (anion-impregnated) chemistries, binding dissociable ions and other charged particles with a very high affinity. In the illustrated embodiment, the resin bed 32 comprises mixed anion- and cation-impregnated resin beads with weakly associated hydrogen or hydroxyl groups, respectively. The ion exchange resins of the preferred embodiment comprise styrene divinyl benzene. Such resins are available, for example, from Rohm & Haas of Philadelphia, Pa. under the trade name IRN 150, or from Sybron of Birmingham, N.J. under the trade name NM60. Cation exchangers exchange hydrogens for any dissolved cations in the diluent. Common dissolved cations include sodium ($Na^+$), calcium ($Ca^{2+}$) and aluminum ($Al^{3+}$). The anion exchange resins exchange hydroxyl ions for any anions present in an aqueous solution. Common anions include chloride ($Cl^-$) and sulfides ($S^{2-}$). The resin bed 32 additionally retains some endotoxins that escape the upstream filtration components. The skilled artisan will recognize other types of ion-exchange resins that could also be utilized in this stage.

The preferred mixed resin bed 32 simplifies and provides a more compact pack 12 than more conventional ion exchange columns, wherein anion and cation exchangers are separated. Moreover, the mixed bed 32 arrangement prevents recharging the ion exchange resin by back-flushing, thus discouraging re-use and maintaining sterility of the unit.

Downstream of the deionization resin bed 32 are a deionization bed restraint 34 and a terminal filter element 36, in sequence. The restraint 34 preferably comprises the same polypropylene mesh utilized for the illustrated depth filter 26 and carbon bed restraint 30. The resin bed restraint 34 serves to prevent passage of deionization bed fragments or fines, as well as any other particulates that have escaped the upstream filters 26, 30. The restraint 34 also serves to protect the filter element 36 downstream of the restraint 34.

The terminal filter element 36 comprises a permeable membrane, preferably a microfiltration or ultrafiltration membrane, depending upon the application. The term "terminal," as utilized in this context, refers to the filtration element with the lowest porosity, and not the physical location. Typically, however, the terminal filter will be immediately adjacent the outlet, as shown, such that large particulates are filtered out by courser filtration elements upstream of the terminal filter. The terminal filter 36 preferably has a porosity of at most about 0.5 μm, and none preferably less than about 0.22 μm.

For applications in remote locations where water is untreated or insufficiently treated, an ultrafiltration membrane is most preferable. Nominal porosity of between about 10,000 and 30,000 molecular weight cut-off desirably filters out viruses prevalent in such locations, such as hepatitis, rota virus, polio, etc. Nominal cut-off for the illustrated embodiment is between about 15,000 and 25,000 MW. While endotoxins (complex lipopolysaccaride) generally aggregate into complexes of greater than about 1,000,000 molucular weight, an ultrafiltration membrane can retain even a single unit of endotoxin (about 15,000 molecular weight).

For employment in more developed locations, where treated water is available (e.g., municipal water in most American cities), the water purification pack 12 need not filter out pathogenic viruses. Accordingly, for such uses the terminal filter 36 comprises a microfiltration membrane. Advantageously, the higher porosity of a microfiltration membrane allows a greater flow rate for a given feed pressure or a lower feed pressure for a given flow rate. The microfiltration membrane preferably has a porosity of lower than about 0.5 μm, and more preferably comprises a 0.22 μm or finer filter, and most preferably has a porosity of about 0.20 μm or finer. Desirably, the terminal filter 36 has enhanced endotoxin binding characteristics and is preferably chemically treated to incorporate a quaternary amine exchanger (QAE) to bind endotoxins. Such endotoxin binding membranes are available under the trade name HP200 from the Pall Specialty Materials Co. Most preferably, the terminal filter 36 comprises two successive QAE-treated 0.20 μm permeable membranes, ensuring adequate endotoxin retention. Despite a high flux rate compared to ultrafiltration membranes, therefore, the terminal filter 36 incorporating a microfiltration membrane removes endotoxins as well as microbes and particulate matter of less than 1 μm from diluent passing therethrough. In fact, challenge water with endotoxin levels as high as 1,000 ng/mL have been purified through the illustrated pack 12 to below the current detection limit (0.006 ng/mL).

The purification stages within the water purification pack are thus such that water passing through the pack 12 and exiting the housing outlet 24 is of a purity level safe for injection into the human body (following the addition of appropriate salts for physiologic solutions). Preferably, effluent water conforms to the purity levels set forth above. It will be understood, of course, that while safe enough for injection, the fluid may actually be employed for alternative medical applications, such as wound irrigation, use in instrument cleaning solutions, and general employment by immuno-comprised individuals (e.g., AIDS patients, geriatrics, etc.).

Desirably, the water purification pack 12 includes an upstream cap 38 over the housing inlet 22, and a downstream cap 40 over the housing outlet 24. The sterility of the purification elements housed within the housing 20 is thus maintained until use. As will be understood in the art, the inlet 22 and outlet 24 can be provided with threads or Luer-type fittings (see FIGS. 8–10) to mate with upstream and downstream elements in the peritoneal dialysate delivery system 10 (FIG. 1).

The sterility and efficacy of the water purification pack 12 is also reinforced by features discouraging re-use of the water pack. As previously noted, the resin bed 32 preferably comprises a mixed bed of anion- and cation-exchangers. Thus, the mixed bed 32 cannot be recharged by traditional backflushing techniques, since regeneration of the cation-exchanger would result in exhaustion of the anion exchanger and vice versa.

Additionally, the water purification pack is preferably configured to irreversibly connect with a downstream collection device. In one preferred arrangement, the housing outlet 24 is welded or otherwise integrally connected with a collection tube leading to a collection bag or other container. When water is purified by passing through the housing 22 and fills the downstream collection container, the preferred plastic tubing is simultaneously cut and cauterized to seal the tube downstream of the outlet 24, preventing re-use of the water pack 12.

Figure 8A:
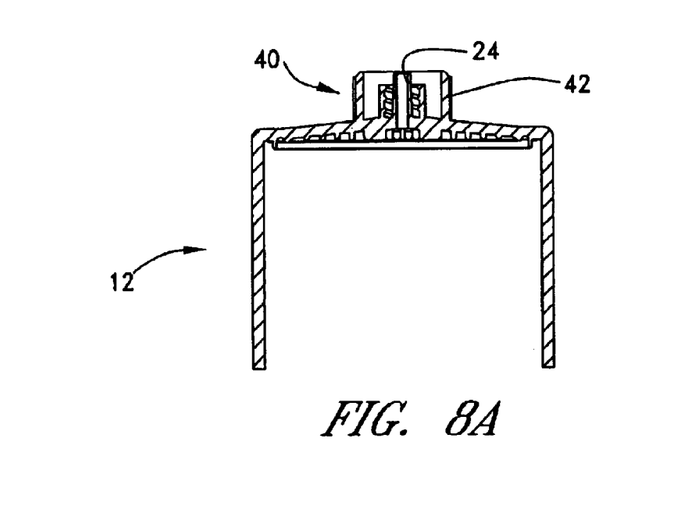
FIGS. 8A and 8B illustrate side sectional and plan views, respectively, of a downstream end of the water purification pack of FIG. 2.
Figure 8B:
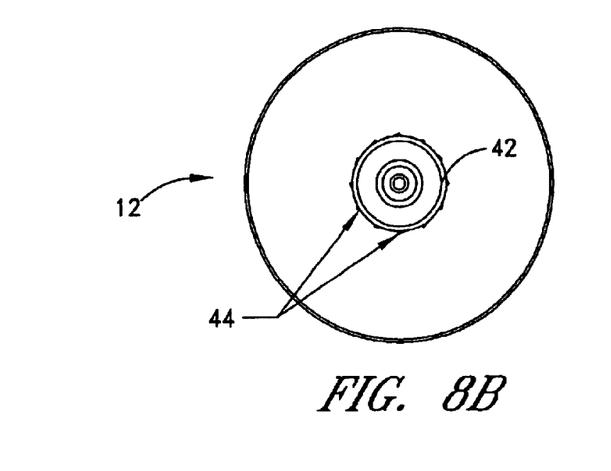
Figure 9A:
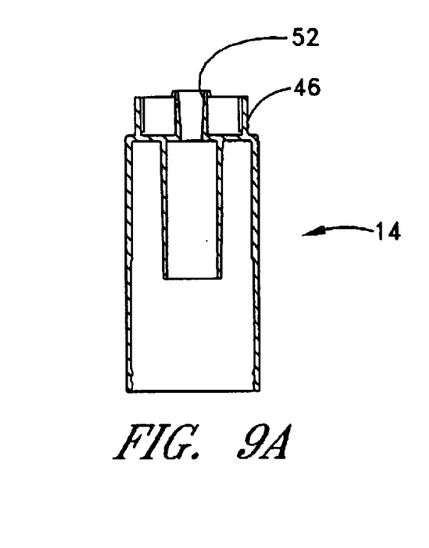
FIGS. 9A and 9B illustrate side sectional and plan views, respectively, of an upstream end of the reagent cartridge of FIG. 3, configured to irreversibly connect with the water purification pack.
Figure 9B:
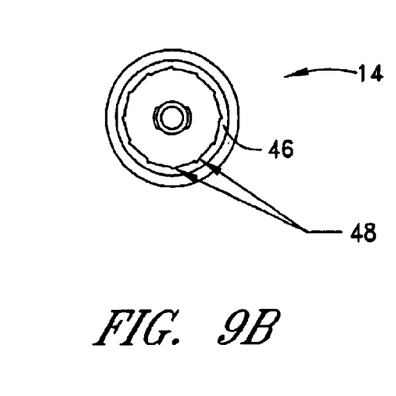

With reference to FIGS. 8 and 9, in another preferred arrangement, the outlet 24 is irreversibly connectable with the downstream reagent cartridge 14. The water pack outlet 24 and the reagent cartridge inlet 52 thus have interlocking mechanisms that are irreversible without damage to the mechanisms.

In the illustrated embodiment, the water pack housing 20 includes a cylindrical collar 42 surrounding the outlet 24, the collar having outer ratcheting teeth 44. The reagent pack 14 includes a similar cylindrical collar 46 surrounding the inlet 52, and the collar 46 includes internal ratchet teeth 48. The outer collar 46 of the reagent pack 14 is sized to fit over the outer collar 42 of the water pack 12. The ratcheting teeth 44, 46 are sloped to slide past each other during clockwise rotation to tighten the inner Luer lock mechanism. The teeth 44, 46 engage one another, however, to prevent counter-clockwise rotation, such that the Luer lock cannot be loosened.

Figure 10:
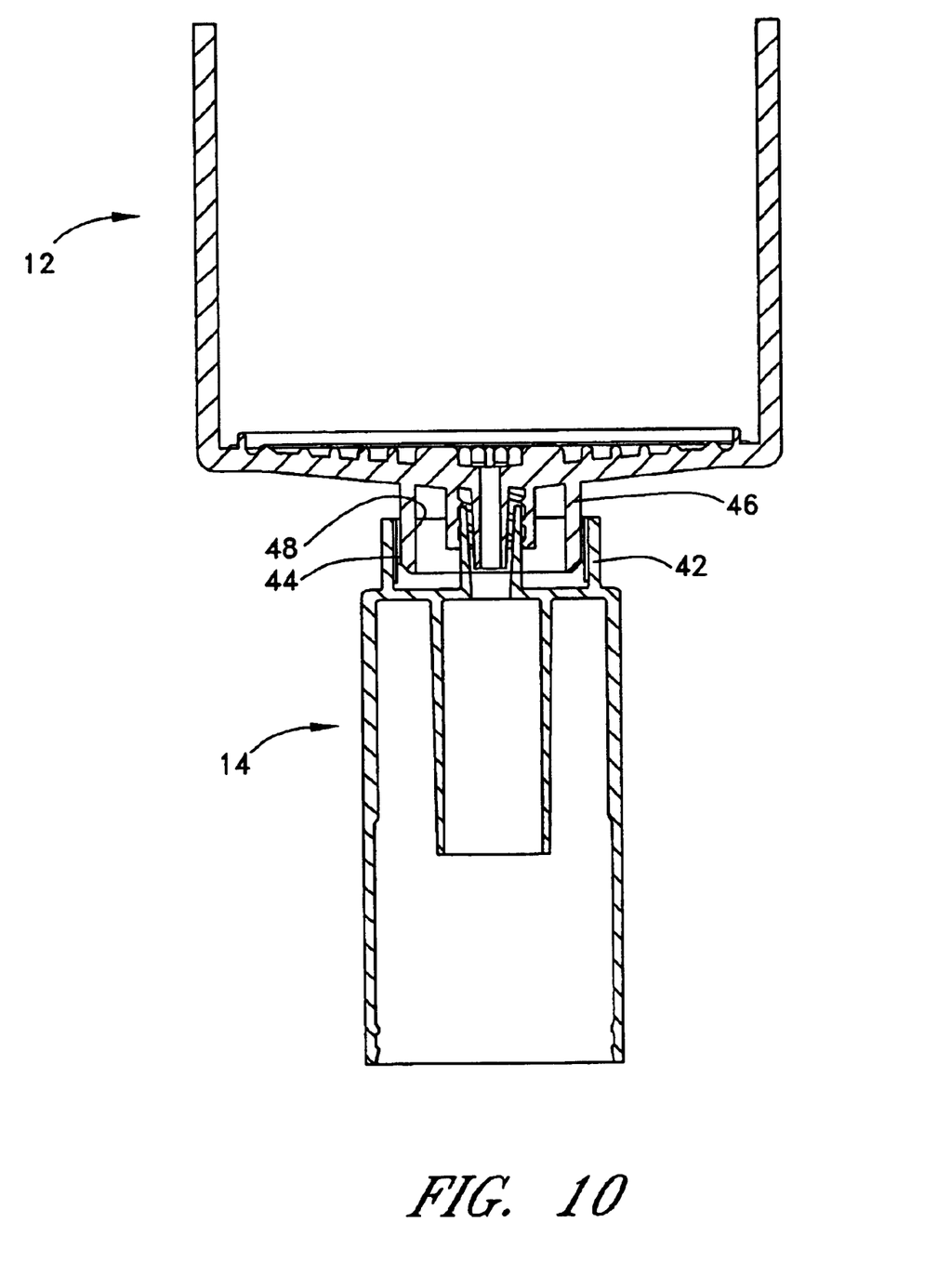
FIG. 10 is a side sectional view of a coupling between the water purification pack and reagent cartridge of FIGS. 8 and 9.

Accordingly, the locking mechanism must be broken or otherwise damaged to separate the used water pack 12 from the reagent cartridge 14. Such damage or breakage minimizes the risk of accidentally re-using a spent water pack 12. The skilled artisan will readily appreciate that similar irreversible locking mechanisms can be utilized with other collection or delivery devices downstream of the water purification pack. The skilled artisan will also recognize other suitable irreversible locking mechanisms for discouraging re-use.

Single-Bed Reagent Cartridge

Figure 3:
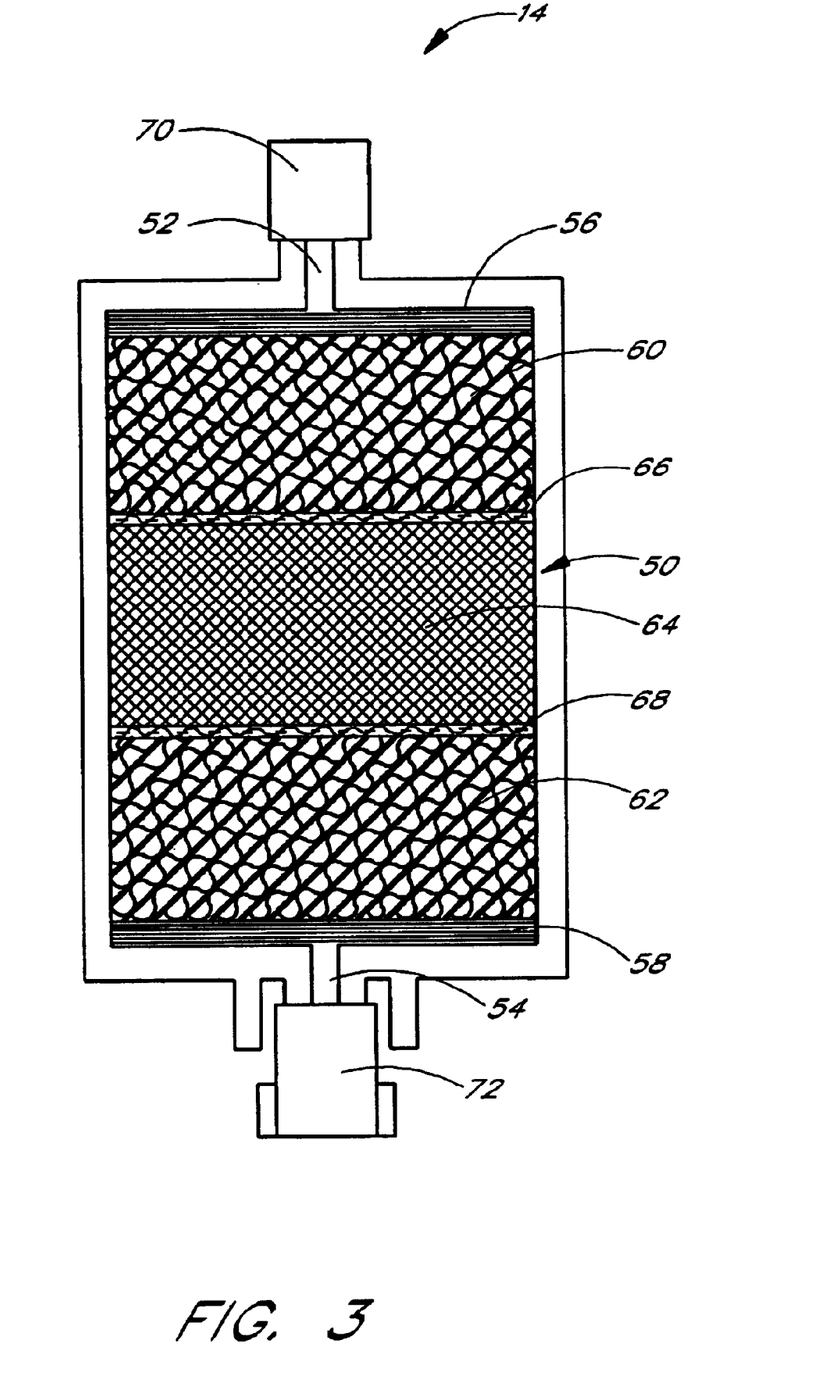
FIG. 3 is a schematic side sectional view of a reagent cartridge for housing reagents of peritoneal dialysate.
Figure 4:
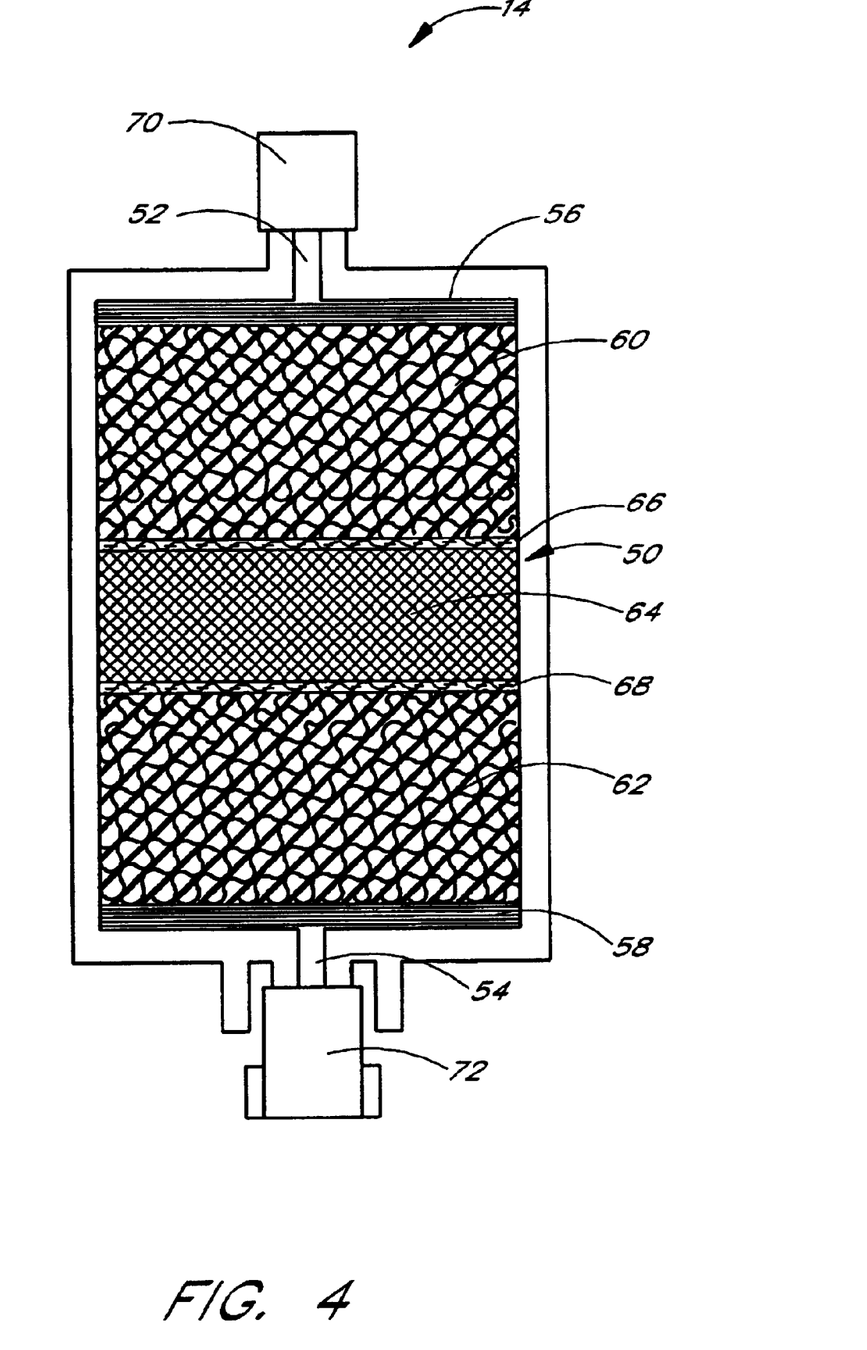
FIG. 4 shows the reagent cartridge of FIG. 3 after partial dissolution of the reagents housed therein.
Figure 5:
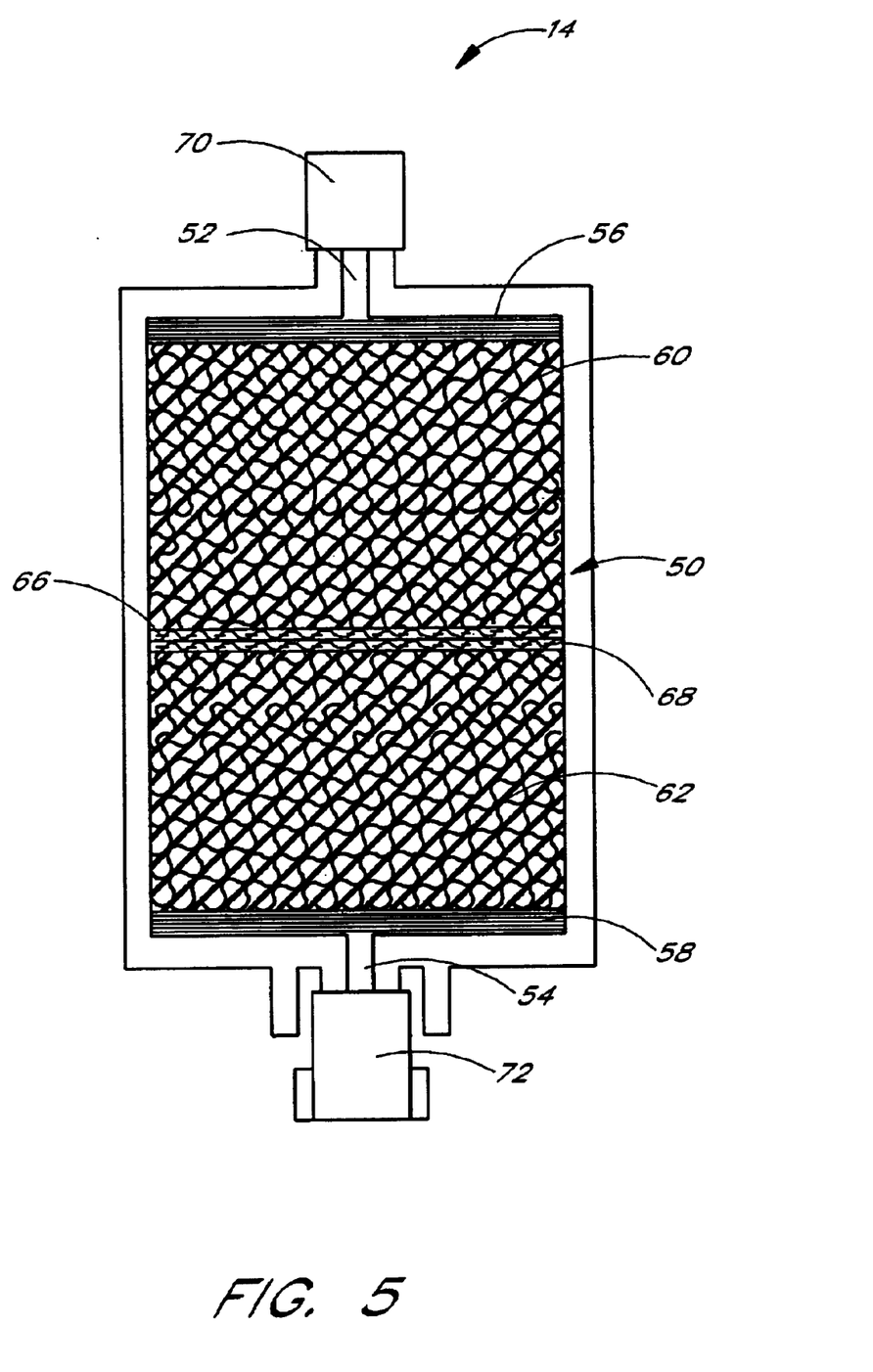
FIG. 5 shows the reagent cartridge of FIG. 3 after complete dissolution of the reagents housed therein.

FIGS. 3–5 illustrate a single-bed reagent cartridge 14 for use with the water purification pack. The figures illustrate various stages of dissolution, as will be better understood from the methods of operation discussed hereinbelow.

FIG. 3 shows a fully charged reagent cartridge 14, in accordance with the first embodiment. The cartridge 14 comprises rigid walled housing 50 with an inlet port 52 at an upstream end, and an outlet port 54 at a downstream end. Within the housing, a number of porous elements define a fluid flow path between the inlet port 52 and the outlet port 54.

The housing 50 is preferably transparent or translucent, advantageously enabling the user to observe the operation of the device and complete dissolution of reagents prior to use of a produced solution, as will be apparent from the discussion of the method of operation, discussed hereinbelow. Examples of translucent and transparent polymers are polypropylene, polycarbonate and many other well-known materials.

Within the housing 50, immediately downstream of the inlet port 52, is an inlet frit 56, which serves as a safety filter to contain any reagent which escapes the restraints described below. An outlet frit 58 serves a similar function immediately upstream of the outlet 54. Desirably, the inlet frit 56 and the outlet frit 58 comprise porous elements having a porosity smaller than the smallest particle of the reagents housed within the cartridge 14. The frits 56, 58 thus serve as filters to ensure that no reagent escapes the cartridge prior to dissolution, as will be described below. An exemplary frit is a multilayered polypropylene laminate, having a porosity between about 1 $\mu$m and 100 $\mu$m, more preferably between about 10 $\mu$m to 50 $\mu$m. Further details on the preferred material are given below, with respect to the reagent restraints.

Downstream of the inlet frit 56 is an upstream reagent compression component 60. Similarly, upstream of the outlet frit 58 is a downstream reagent compression component 62. The compression components 60, 62 preferably comprise materials that have sponge-like elasticity and, as a result of compression, exert axial pressure while trying to return to its original, expanded form. The compression components 60, 62 preferably comprise compressible, porous, open cell polymer or foam, desirably more porous than the frits, to avoid generation of back pressure. An exemplary material for the compression components is a polyurethane foam. Desirably, the compression components 60, 62 and surrounding housing 50 are arranged such that the compression components 60, 62 exert a compressive force on the reagent bed regardless of the size of the reagent bed. In other words, the compression components 60 and 62 would, if left uncompressed, together occupy a greater volume than that defined by the housing 50. Desirably, the pressure exerted is between about 50 grams per sq. inch and 2,000 grams per sq. inch, more preferably between about 300 grams per sq. inch and 900 grams per sq. inch.

It will be understood that, in other arrangements, metal or polymer coiled springs and porous plates can serve the same function. Such alternative compression components are disclosed, for example, with respect to FIGS. 12–15; Col. 9, lines 8–53 of U.S. Pat. No. 5,725,777, the disclosure of which is incorporated herein by reference. Another preferred compression component is disclosed in U.S. provisional application No. 60/132,088, filed Apr. 30, 1999, the disclosure of which is hereby incorporated by reference. It will also be understood, in view of the discussion below, that a single compression component can serve the function of the illustrated two compression components. Two components exerting pressure on either side of a reagent bed 64 (described below), however, has been found particularly advantageous in operation.

A single reagent bed 64 is situated between the compression components 60, 62. The reagent bed 64 is desirably sandwiched between an upstream reagent restraint 66 and a downstream reagent restraint 68. The upstream reagent restraint 66 is thus positioned between the reagent bed 64 and the upstream compression component 60, while the downstream reagent restraint 68 is positioned between the reagent bed 64 and the downstream compression component 62.

The restraints 66, 68 desirably prevent the passage of reagent particles in their dry formulation. The porosity of the restraints is therefore selected to be less than the size of the smallest particles within the reagent bed, depending upon the particular reagent formulations and physical particle size desired. Desirably, the pores are large enough to avoid excessive pressure drop across the restraints. Preferably, the restraint porosity in the range between about 1 $\mu$m and 100 $\mu$m, more preferably between about 10 $\mu$m to 50 $\mu$m. An exemplary restraint, suitable for the illustrated peritoneal dialysis application, comprises the same material as the frits 56, 58, and consists of a non-woven polymer, particularly polypropylene with a porosity of about 20 microns. Another exemplary restraint comprises sintered polyethylene with a porosity of about 30 microns.

Additionally, the restraints 66, 68 are sized and shaped to extend completely across the housing 50, forming an effective seal against reagent particulates escaping around the restraints 66, 68.

The reagent bed 64 comprises a complete formulation of dry or lyophilized reagents required to produce a peritoneal dialysis solution. In the illustrated single-bed embodiment, the reagent bed 65 is a mixture of compatible reagents, such as will not exhibit spontaneous chemical reaction from prolonged contact in their dry form. Accordingly, a buffering agent such as an acetate or lactate, and particularly sodium lactate, is employed in place of a bicarbonate. Further reagents include electrolytes, such as sodium chloride, magnesium chloride, potassium chloride and calcium chloride; a sugar, preferably dextrose; and an acid, particularly citric acid. Advantageously, the acid component of the reagent bed 65 can be lower than conventional solutions, since storage in dry form alleviates the tendency for dextrose caramelization.

The illustrated housing 50 holds reagents sufficient to produce 2 liters of a typical peritoneal dialysate solution. Accordingly, the reagent bed 64 holds the following reagents:

TABLE I

| Dry Reagent Constituents | Mass | Dry Volume |
| --- | --- | --- |
| Calcium chloride | 514 mg | Negligible |
| Magnesium chloride | 101.6 mg | Negligible |
| Sodium lactate | 8.96 g | 24 mL |
| Sodium chloride | 10.76 g | 22 mL |
| Dextrose | 50 g | 70 mL |
| Total | 70 g | 116 mL |

The dry volume of the above-listed reagents, which can produce 2 L of 2.5% dextrose peritoneal dialysate, is thus about 100 mL. The housing 50 for such a formulation need only be about 125% to 500% of the dry reagent volume, more preferably about 150% to 200%, depending upon the selected compression components 60, 62. The illustrated housing 50 is about 2" in diameter and about 3" in height, thus occupying about 175 mL. The cartridge 14 thus represents a much smaller and more stable form of dialysate for storage and transport, compared to 2 L of prepared solution. If a smaller or larger volume of solution is desired, the skilled artisan can readily determine the proportionate weight and volume of dry reagents required in the reagent bed 64, such as for producing 1 L, 3 L, 6 L, 10 L, etc. Similarly, the skilled artisan can readily determine the proportions of reagents desirable for 1.5% dextrose dialysate, 4% dextrose dialysate, etc.

An inlet port cover 70 and an outlet port cover 72 cover the housing inlet port 52 and outlet port 54, respectively. The port covers 70, 72 advantageously seal out moisture and prevent destabilization of the dry reagents housed within during transport and storage. As with the water purification pack, the inlet port 52 and outlet port 54 can be configured with threaded or Luer-type connection fittings. In the illustrated embodiment, the inlet port 52 is configured to mate with the outlet 24 of the water purification pack 12 (FIG. 2), while the outlet port 54 is configured to mate with the downstream tube 18 (see FIG. 1).

Double-Bed Reagent Cartridge

Figure 6:
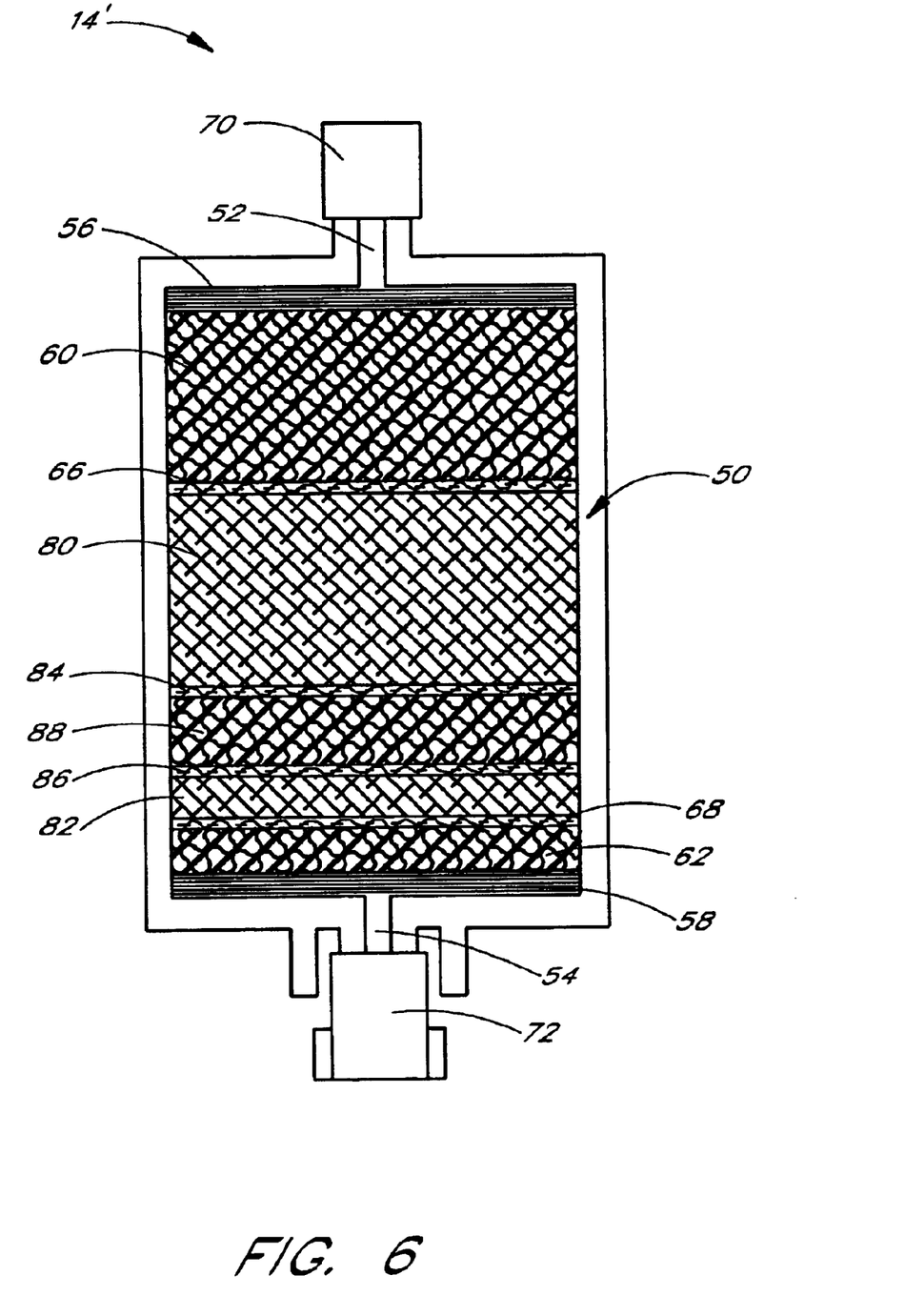
FIG. 6 is a schematic side sectional view of a reagent cartridge for housing reagents of peritoneal dialysate.
Figure 7:
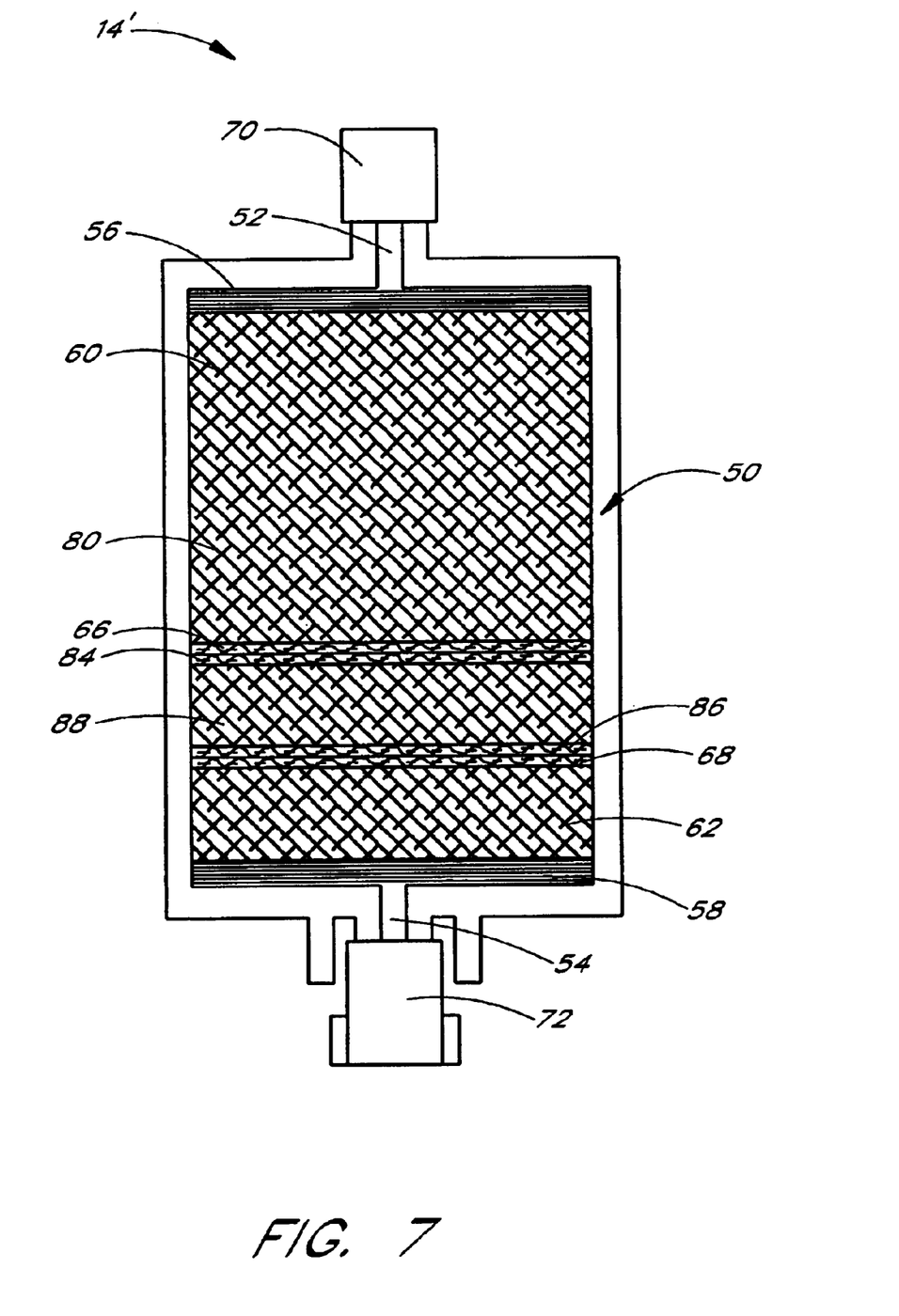
FIG. 7 shows the reagent cartridge of FIG. 6 after complete dissolution of the reagents housed therein.

FIGS. 6 and 7 illustrate a double-bed reagent cartridge 14'. FIGS. 6 and 7 illustrate the cartridge 14' in fully charged and fully depleted conditions, respectively, as will be better understood from the methods of operation discussed hereinbelow.

With reference initially to FIG. 6, the housing 50 of the double-bed reagent cartridge 14' is preferably similar to that of the first embodiment, such that like reference numerals are used to refer to like parts. Thus, the housing 50 defines an inlet port 52 and outlet port 54, and contains porous elements between the inlet port 52 and outlet port 54, such as to define a fluid flow path through the housing 50. Specifically, the housing 50 contains an upstream frit 56, upstream compression component 60, upstream reagent restraint 66, downstream reagent restraint 68, downstream compression component 62 and downstream frit 58. Each of these elements can be as described with respect to the previous embodiment.

Unlike the single-bed cartridge 14 of FIGS. 3–5, however, multiple reagent beds are confined between the upstream restraint 66 and downstream restraint 68. In particular, a primary reagent bed 80 and a secondary reagent bed 82 are shown in the illustrated embodiment, separated by at least one restraint. In the illustrated embodiment, the reagent beds 80 and 82 are separated by a first intermediate restraint 84 and second intermediate restraint 86, as well as an intermediate compression component 88 between the intermediate restraints 84 and 86.

Accordingly, the primary reagent bed 80 is confined between upstream restraint 66 and the first intermediate restraint 84, while the secondary reagent bed 84 is similarly confined between the second intermediate restraint 86 and the downstream restraint 68. The intermediate reagent bed restraints 84, 86 desirably serve to contain the reagents within the beds 80, 82 in their dry form, while still being porous enough to allow diluent, along with any dissolved reagents, to pass through. Accordingly, the intermediate reagent restraints 84, 86 can have the same structure as the frits 56, 58 and upstream and downstream reagent restraints 66, 68, as described above with respect to the single-bed embodiment. Similarly, the intermediate compression component 88 can have the same structure as the upstream and downstream compression components 60, 62.

Each of the intermediate compression component 88 and the intermediate reagent restraints 84, 86 are interposed between and separate the primary reagent bed 80 from the second reagent bed 82. Due to the selected porosity of the elements, particularly the intermediate restraints 84, 86, constituents of the two reagent beds 80, 82 therefore do not interact with one another in their dry states.

The illustrated double-bed embodiment therefore enables separate storage of different reagents within the same housing 50. A complete formulation of the dry reagents required to produce a peritoneal dialysis solution may contain reagents that react undesirably when exposed to one other for prolonged periods of time, in either dry or liquid forms, as noted in the Background section. For example, bicarbonates are preferred, physiologically compatible buffering agents for peritoneal dialysis, but tend to be very reactive with typical salts in the dialysate formulation, such as calcium chloride or magnesium chloride. The reactions form insoluble calcium carbonate or magnesium carbonate, and also liberate $CO_2$. Because of the potential reactivity of incompatible reagents, it is preferable to separately store these reagents within the device housing 50.

Separate storage is accomplished by separating reagents into compatible groupings, which are then placed in separate compartments within the housing. The compartments are represented, in the illustrated embodiment, by the primary reagent bed 80 and the secondary reagent bed 82. The potentially reactive reagents are thereby constrained from movement through the housing, when maintained in their dry form, by reagent bed restraints 66, 84, 86, 68 at the upstream and downstream ends of each of the reagent beds 80, 82. As noted above, the reagent bed restraints 66, 84, 86, 68 have fine enough porosity to prevent the passage of reagent particles in their dry form.

In the illustrated embodiment, the primary reagent bed 80 is a reagent mixture, preferably comprising: electrolytes, particularly sodium chloride, potassium chloride, calcium chloride and magnesium chloride; a sugar, particularly dextrose. In other arrangements, the primary reagent bed 80 can also comprise a buffer.

The secondary reagent bed 82 can contain at least one component that is unstable in the presence of at least one component in the primary reagent bed 80. Advantageously, the secondary reagent bed 82 contains a bicarbonate, such as sodium bicarbonate. Because the bicarbonate is separated from calcium chloride and magnesium chloride, the reagents do not react to form insoluble precipitates.

The skilled artisan will readily appreciate that, in other arrangements, the primary reagent bed 80 can contain the bicarbonate if the secondary bed 82 contains calcium chloride and/or magnesium chloride. In still other alternatives, other incompatible reagents for medical solutions can be similarly separated into reagent beds within the same housing. Moreover, three or more reagent beds can be utilized to separate multiple incompatible reagents.

The illustrated housing 50 holds reagents sufficient to produce 2 liters of a typical peritoneal dialysate solution. Accordingly, the reagent beds 80, 82 hold the following reagents:

TABLE II

|  | Mass | Dry Volume |
| --- | --- | --- |
| Primary Reagent Bed | | |
| Calcium chloride | 514 mg | Negligible |
| Magnesium chloride | 101.6 mg | Negligible |
| Sodium chloride | 10.76 g | 22 mL |
| Dextrose | 50 g | 70 mL |
| Subtotal | 61 | 92 mL |
| Secondary Reagent Bed | | |
| Sodium bicarbonate | 6.64 g | 6.1 mL |
| Total | 68 g | 98 mL |

The dry volume of the above-listed reagents, which can produce 2 L of 2.5% dextrose peritoneal dialysate, is thus about 98 mL. As with the previously described single-bed embodiment, the total volume of the cartridge 14' is preferably between about 125% and 500%, and more preferably 150% and 200%, of the dry reagent volume. As also noted above, the skilled artisan can readily determine the proportionate weights and volumes of dry reagents required for forming other peritoneal dialysate solutions, such as 1.5% dextrose dialysate, 4% dextrose dialysate, etc.

Notably, the double-bed cartridge utilizes bicarbonate as the buffer, and omits the need for physiologically damaging acid by enabling production of a physiologic solution.

Method of Operation

In operation, purified diluent is provided to a reagent cartridge 14 or 14', which is fully charged with an appropriate amount of dry reagent, as set forth above. Fluid to be purified (e.g., municipal tap water) is provided to the system 10 of FIG. 1, such that the purified diluent is produced on site and need not be produced remotely and transported, significantly reducing the cost of transportation.

Accordingly, with reference to FIG. 2, diluent in the form of available water is first provided to water purification pack 12 of FIG. 2. Pressure commonly found in municipal water systems is sufficient to feed the water through the purification pack 12. Alternatively, a hand pump or large syringe can be supplied with a measured volume of water, and water hand-pumped therefrom into the purification pack 12. Feed pressure is preferably less than about 20 psi. Fluid flux through the purification pack 12 (with a feed pressure of about 5–10 psi) is preferable at least about 30 mL/min, and more preferably at least about 90 mL/min through the pack 12.

The diluent enters the inlet 22 and passes through depth filter 26, where particulates larger than about 1 micron are filtered out. The depth filter 26 retains insoluble particulates and microbes greater than the pore sizes of the successive layers in this component. Depth filtration is extremely effective in removing contaminants such as asbestos fibers and similarly sized particles.

Filtered diluent continues downward through organic filtration stage 28, where residual organics such as endotoxins and additives such as chlorine, chloramine and trihalomethanes are adsorbed. Additionally, some inorganic materials are removed in the process. Carbon is effective at adsorbing many types of chemicals, it is especially known for its power in adsorbing organic compounds. Carbon's particular affinity for organics is due to its non-polar nature. Carbon is also somewhat effective in adsorbing metals and other inorganics. The illustrated resin has similar absorption characteristics.

After being additionally purified by the organic filtration stage 28, the partially purified diluent passes through the restraint 30 and into the ion-exchange resin bed 32. Dissociated ions and other charged particulates in solution bind to the resins. Some endotoxins that have escaped the upstream components are also retained in the resin bed 32.

After passing through the resin bed restraint 34, which retains the contents of the resin bed 34, the diluent is further purified through the terminal filter element 36. In one embodiment, as previously noted, the terminal filter 36 comprises an ultrafiltration membrane with a nominal cut-off of between about 10,000 and 30,000 molecular weight. Depending upon the density of pores, 5–10 psi feed pressure can produce a flux of between about 35 mL/min and 100 mL/min through such an ultrafiltration membrane. In another embodiment, the filter 36 comprises at least one and preferably two microfiltration membranes of a very fine porosity (e.g., about 0.22 μm or finer), each including chemical treatment with a quaternary amine exchanger for binding residual endotoxins. The flux rate for a device with the microfiltration membrane can be more that twice that of an ultrafiltration membrane with equivalent pore density.

The multiple filtration and chemical binding components of the water purification pack 12 thus ensure removal of particulate, ionic and organic contaminants from the diluent as it passes through the pack 12. Endotoxins, including organic matter such as cell walls from dead bacteria, can be particularly toxic. Highly purified diluent, sufficient to comply with or exceed FDA and U.S. Pharmacopoeia water quality standards for "sterile water for injection," exits the outlet 24, but without the need for reverse osmosis.

With reference to FIG. 1 again, purified diluent then passes from the water purification pack 12 to a collection/delivery device. As noted above, in one embodiment, the downstream device can comprise a simply storage container, such as a plastic bag. In the illustrated embodiment, the storage/delivery device comprises the reagent cartridge 14. Desirably, the downstream storage/delivery device is irreversibly fixed to the water pack outlet 24, either integrally or through a locking mechanism.

FIGS. 3–5 illustrate dissolution of dry reagent 64 as diluent passes through the single-bed reagent cartridge 14 for the peritoneal dialysis. While illustrated cross-sectionally, it will be understood that the preferred transparent or translucent housing 50 enables the user to similarly observe dissolution of the reagent bed 64 as solvent or diluent passes therethrough. Additionally, the user can observe whether insoluble precipitates are present within the reagent bed, prior to employing the cartridge 14. Advantageously, gravitational force is sufficient to draw the water through the cartridge 14.

Referring initially to FIG. 3, purified diluent enters the cartridge 14 through the inlet port 52. Preferably, purified diluent is fed directly from the water purification pack 12. "Directly," as used herein, does not preclude use of intermediate tubing, etc, but rather refers to the fact that water is purified on site immediately prior to solution formation, rather remotely produced and shipped. It will also be understood, however, that the illustrated reagent cartridge will have utility with other sources of sterile diluent.

The diluent passes through the porous inlet frit 56 and the upstream compression component 60. In the illustrated embodiment, the compression component 60 is a porous, open-celled foam, which readily allows diluent to pass therethrough. The diluent then passes through the upstream reagent restraint 66 to reach the dry reagent bed 64. In addition to retaining the dry reagents in the bed 64, the frit 56 and restraint 66 facilitate an even distribution of water flow across the sectional area of the housing 50.

As the solution passes through interstitial spaces in the bed 64, the dry reagents are eroded, preferably dissolved, and carried by the diluent through the downstream reagent restraint 68, the downstream compression component 44 and the outlet frit 58, exiting through outlet 24. The solution passes through the tube 18 into the collection reservoir 16 (see FIG. 1) and then into the peritoneal cavity of a patient.

Referring to FIG. 4, as the reagents are dissolved, the volume of the reagent bed 64 is reduced, as can be seen from a comparison of FIG. 4 with FIG. 3. The compression components 60, 62 apply continuous compressive force on either side of the reagent bed 64. As dry reagent is dissolved, the compressive force packs the reagents close together. Such continuous packing prevents expansion of interstitial spaces as the reagent particles are dissolved. Without the compressive force, the interstitial spaces between the reagent particles tend to expand into larger channels within the reagent bed 64. These channels would serve as diluent flow paths, which would permit a large volume of diluent to flow through the bed 64 with minimal further dissolution. Significant portions of the bed would be by-passed by these channels, and dissolution would be slow and inefficient. Applying continuous compression to the beds minimizes this problem by continuously forcing the reagent particles together as the bed dissolves, ensuring continuous, even exposure of the diluent to the reagents of the bed 64.

Though two compression components 60, 62 are preferred, thus compressing the reagent bed 64 from two sides, it will be understood that a single compression component can also serve to keep the regent beds 64 compacted. Moreover, though illustrated in an axial arrangement, such that diluent flows through the compression components 60, 62, it will be understood that the compression components can exert a radial force in other arrangements.

The compressive force of the preferred compression components 60, 62, exerted evenly across the housing 50, additionally aids in maintaining the planar configuration of the reagent restraints 66, 68 on either side of the reagent bed 64, even as the compression components 60, 62 move the restraints inwardly. The restraints 66, 68 thus continue to form an effective seal against the housing sidewalls, preventing dry reagent particulates from escaping the bed 64 until dissolved.

With reference to FIG. 5, dissolution continues until the reagent bed is depleted and the restraints 66, 68 contact one another. Diluent can continue to flow through the housing 50 into the reservoir 16 (FIG. 1) until the appropriate concentration of peritoneal dialysate solution is formed. For example, in the illustrated embodiment, 2 liters of diluent should be mixed with the contents of the reagent bed 64. Accordingly, 2 liters of diluent are passed through the housing 50. The contents are typically fully dissolved by the time about 1.5 liters has passed through the housing, but diluent can continue to flow until the appropriate final concentration is reached in the reservoir. Alternatively, a concentrate can be first formed and independently diluted.

Advantageously, the illustrated apparatus and method can form peritoneal dialysis solution simply by passing water through the cartridge 50, without complex or time consuming mixing equipment. The solution can thus be formed on-site, immediately prior to delivery to the peritoneal cavity, such that the dialysate need not be shipped or stored in solution form. Accordingly, a low acid level is possible without undue risk of dextrose carmelization. Conventionally, a pre-formed dialysis solution formed has a pH between about 4.0 and 6.5, and the exemplary reagent mix of Table I produces a conventional solution with pH of about 5.2. Solution produced from the illustrated single-bed cartridge of FIGS. 3–4, however, can have lower acidity, since dextrose does not sit in solution for extended periods of time. Accordingly the pH level is preferably between about 6.0 and 7.5, more preferably about 7.0.

Referring to FIGS. 6 and 7, the double-bed reagent cartridge 14' operates in similar fashion. Purified diluent is fed to the housing inlet 52, and passes through the inlet frit 56, the upstream compression component 60, the upstream restraint 66, and into the primary reagent bed 80. Dissolution of reagents in the primary bed 80 forms a solution which passes on through the first intermediate restraint 84, the intermediate compression component 88 and the second intermediate restraint 86. Reagents in the secondary bed 82 then also dissolve into the diluent, and the enriched solution continues on through the downstream reagent restraint 68, the downstream compression component 62 and the outlet frit 58. A complete solution thus exits the outlet port 54.

As in the previous embodiment, the regent beds 80, 82 are continually compressed as the reagents dissolve. Use of three compression components 60, 88, 62 has been found to improve dissolution by compressing each bed 80, 82 from two sides. The skilled artisan will understand, however, that two compression components, in the positions of the upstream and downstream third components, can adequately serve to keep the reagent beds compressed enough to aid the rate of dissolution, particularly if provided with a high degree of elasticity. Similarly, a single intermediate compression component, in the position of the illustrated intermediate compression component 88, can accomplish this function, while advantageously also separating the incompatible reagent beds. Additionally, the compression component need not be axially aligned with the reagent beds, but could instead surround or be surrounded by the reagent beds, in which case the compression components would preferably be outside the diluent flow path.

Advantageously, the illustrated embodiments provide stable, dry forms of peritoneal dialysis solutions. Storage and transport of the reagent cartridges of the illustrated embodiments represents considerable cost savings over storage and transport of prepared peritoneal dialysate solutions. Dry or lyophilized reagents are moreover more stable than solution, and therefore less harmful to the patient.

While the storage and transport of dry reagents is generally recognized as advantageous, practical application has been difficult. The described embodiments not only provide transport and storage, but additionally provide integrated mechanisms to ensure complete dissolution of the dry reagents. Continuous compression of the reagent bed(s) during dissolution, combined with the transparent windows allowing real time viewing of the dissolution, ensure rapid, complete and verifiable dissolution of the reagents. Thus, the preferred embodiments can be utilized on site, even in the home, without requiring complex mixing and/or analytical tools.

Moreover, the illustrated embodiments facilitate a wider practicable range of reagents. For example, physiologically compatible bicarbonate can be employed along with calcium and magnesium. Separate storage and solution preparation only immediately prior to administration enables this combination. High dextrose solutions, as appropriate for peritoneal dialysis, can be employed without acidic buffers, such that physiologically compatible pH levels can be practically obtained, preferably between about 4.0 and 7.5, and more preferably between about 6.0 and 7.5. The reagents listed in Table II produce a solution with a pH of about 7.0.

The illustrated fluid purification pack 12 is also a compact, conveniently transportable device that facilitates on-site production of injectable quality fluid from available fluid. Advantageously, despite a small size and low feed pressure, the pack 12 rapidly provides on-site, injectable quality water as input water flows linearly from inlet to outlet. A permeable terminal filter 36, represents the lowest porosity element in the pack 12. In contrast to semi-permeable, osmotic membranes, this element facilitates this high flux at low pressures while still retaining extremely fine particles and toxins.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the dependent claims.

I claim:

1. A method of producing injectable quality of water, comprising:
   providing a portable purification pack comprising a housing surrounding a plurality of purification elements in series;
   providing non-sterile water to an inlet of the housing under a feed pressure of less than about 20 psi;
   passing the water through the plurality of purification elements; and
   outputting purified water from an outlet of the housing, wherein the purified water has an organic content, conductivity, pH level and particulate contamination level suitable for injection into the human body.

2. The method of claim 1, further comprising injecting the purified water into a human body.

3. The method of claim 2, further comprising dissolving reagents within the purified water prior to injecting the purified water into the human being.

4. The method of claim 3, wherein dissolving reagents in the purified water comprises passing the purified water from the outlet into a drug reagent cartridge housing dry formulations suitable for forming a medical treatment solution.

5. The method of claim 4, wherein the medical solution comprises peritoneal dialysate.

6. The method of claim 1, wherein outputting the purified water has a flux rate of greater than about 30 mL/min.

7. The method of claim 6, wherein outputting the purified water has a flux rate of greater than about 100 mL/min.

8. The method of claim 7, wherein the feed pressure is between about 5 psi and 10 psi.

9. The method of claim 1, wherein the plurality of purification elements comprises a terminal filter having a porosity of no more than about 0.5 µm.

10. The method of claim 1, wherein the purified water has a total organic content of less than about 500 ppb; conductivity of less than about 2.0 µ Siemens; pH between about 4.5 and 7.5; fewer than about 12 particles/mL of particles greater than 10 µm; fewer than about 2 particles/mL of particles greater than 25 µm; and lower than about 0.025 ng/mL of endotoxins.

11. A method for producing fluid for medical application, comprising:
    providing a portable housing;
    passing non-sterile fluid through the housing;
    retaining particulate contamination, organic matter, dissociated ions, and endotoxins from the feed fluid within purification elements in the housing; and
    outputting fluid suitable for medical applications from the housing.

12. The method of claim 11, wherein the purification elements include a mixed bed of anion-exchange and cation-exchange resins.

13. The method of claim 12, wherein the purification elements further comprise a depth filtration stage and an organic adsorption stage.

14. The method of claim 11, wherein retaining endotoxins comprises passing the feed fluid through a permeable membrane treated with a quaternary amine exchange chemistry.

15. The method of claim 14, wherein retaining endotoxins comprises passing the feed fluid through a permeable ultrafiltration membrane having a nominal cut-off porosity of between about 10,000 and 30,000 molecular weight.

16. The method of claim 11, wherein retaining particulate contamination comprises passing the feed fluid through a depth filtration stage.

17. The method of claim 11, wherein the housing contains an outlet including an irreversible lock.

18. method for producing fluid for medical application, comprising:
    providing a portable housing;
    passing non-sterile fluid through the housing;
    retaining particulate contamination, organic matter, dissociated ions, and endotoxins from the feed fluid within purification elements in the housing, the purification elements arranged in series; and
    outputting fluid suitable for medical applications from the housing.

19. The method of claim 18, wherein the purification elements include a mixed bed of anion-exchange and cation-exchange resins.

20. The method of claim 19, wherein the purification elements further comprise a depth filtration stage and an organic adsorption stage.

* * * * *